US00PP17011P3

(12) United States Plant Patent
Takamura et al.

(10) Patent No.: US PP17,011 P3
(45) Date of Patent: Aug. 15, 2006

(54) ***VERBENA* PLANT NAMED 'SUNMARIBAGADI'**

(50) Latin Name: *Verbena hybrida*
Varietal Denomination: Sunmaribagadi

(75) Inventors: Naoto Takamura, Omihachiman (JP); Tomoya Misato, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 59 days.

(21) Appl. No.: 10/812,500

(22) Filed: Mar. 29, 2004

(65) Prior Publication Data

US 2005/0216992 P1 Sep. 29, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP11,104 P 10/1999 Yomo et al.

FOREIGN PATENT DOCUMENTS

| | | |
|---|---|---|
| JP | PBR 8148 | 6/2000 |
| JP | PBR 10647 | 9/2002 |

*Primary Examiner*—Anne Marie Grunberg
*Assistant Examiner*—Georgia Helmer
(74) *Attorney, Agent, or Firm*—Christie, Parker & Hale, LLP

(57) ABSTRACT

Disclosed herein is a new and distinct variety of *Verbena* plant having a decumbent growth habit. The *Verbena* plant has abundant branching, the whole plant remaining in bloom for a considerable period of time. The flowers are formed in profusion in a cluster and the petals display a dark purplish red color. The blooming period is from April to November, and the flowering duration is long. The plant exhibits high tolerance to heat, and high resistance to rain, pests and disease, particularly powdery mildew.

2 Drawing Sheets

Botanical classification: *Verbena hybrida.*
Varietal denomination: 'Sunmaribagadi'.

BACKGROUND OF THE VARIETY

The present invention relates to a new variety of *Verbena* plant, named 'Sunmaribagadi' that originated from open-pollination of a *Verbena* hybrid variety called 'H116-1' (unpatented).

The *Verbena* is a very popular plant and is used for flower bedding and potting in the summer season. There are only a few varieties of *Verbena* plants having a decumbent growth habit, abundant branching, many flowers in a cluster, and a high resistance to heat, rain, and disease. Accordingly, this invention was aimed at obtaining a new variety having a decumbent growth habit, much branching, many dark reddish purple flowers in a spike, high tolerance to heat and rain, and resistance to disease and pests.

The female parent 'H116-1' used in the open-pollination of 'Sunmaribagadi' is a strain of our breeding lines. The stem of 'H116-1' is longer than that of 'Sunmaribagadi', and the petal color of 'H116-1' is purplish red, while that of 'Sunmaribagadi' is dark purple-red.

In October 2000, 50 seedlings were obtained from the natural crosses of *Verbena* variety called 'H116-1' and were grown in a controlled environment at Yokaichi-shi, Shiga-ken, Japan. These seedlings were grown in pots in glass-houses for evaluation. One seedling was selected in view of its growth habit and flower color in October 2001. That seedling was propagated by cutting and a trial was carried out by flower potting and bedding from April to October 2002. The botanical characteristics of that plant were then examined, using similar varieties 'Sunmariwaba' (U.S. Plant Pat. No. 11,104) and 'Sunmariro' (U.S. Plant Pat. No. 14,306) for comparison. As a result, it was concluded that this *Verbena* plant is distinguishable from any other variety, whose existence is known to us, and uniform and stable in its characteristics. The new variety of *Verbena* plant was named 'Sunmaribagadi'.

In the following description, the color-coding is in accordance with The Horticultural Colour Chart of The Royal Horticultural Society, London, England (R.H.S.).

SUMMARY OF THE VARIETY

This new variety is unlike any commercially available *Verbena* variety known to us as evidenced by the following unique combinations of characteristics.

1. Decumbent growth habit with abundant branching.
2. Plentiful number of flowers in a spike having great profusion of blooms with the entire plant remaining in bloom for a considerable period of time.
3. Long flowering duration.
4. The petal color is dark purplish red (near R.H.S. 59A).
5. The plant has a high resistance to rain, heat, disease and pests.

The new variety 'Sunmaribagadi' differs from the similar variety 'Sunmariwaba' in the following points.

1. The plant height of 'Sunmaribagadi' is higher than that of 'Sunmariwaba'.
2. The internode length of 'Sunmaribagadi' is shorter than that of 'Sunmariwaba'.

3. The leaf of 'Sunmaribagadi' is narrower than that of 'Sunmariwaba'.
4. The spike length of 'Sunmaribagadi' is shorter than that of 'Sunmariwaba'.
5. The flower color of 'Sunmaribagadi' is dark purplish red (near R.H.S. 59A), while that of 'Sunmariwaba' is strong purplish red (near R.H.S. 71A) with a small eye.
6. The calyx of 'Sunmaribagadi' is shorter than that of 'Sunmariwaba'.

The new variety 'Sunmaribagadi' differs from the similar variety 'Sunmariro' in the following points.

1. The plant size of 'Sunmaribagadi' is more compact than that of 'Sunmariro'.
2. The internode length of 'Sunmaribagadi' is shorter than that of 'Sunmariro'.
3. The leaf of 'Sunmaribagadi' is narrower than that of 'Sunmariro'.
4. The spike length of 'Sunmaribagadi' is shorter than that of 'Sunmariro'.
5. The flower color of 'Sunmaribagadi' is dark purplish red (near R.H.S. 59A), while 'Sunmariro' is vivid red (near R.H.S. 77B).

This new variety of *Verbena* plant 'Sunmaribagadi' was asexually reproduced by the use of cuttings at Yokaichi-shi, Shiga-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during April 2003 while growing outdoors in 30 cm pots at an age of approximately 6 months at Yokaichi-shi, Shiga-ken, Japan.

DESCRIPTION OF THE VARIETY

Figure 1:
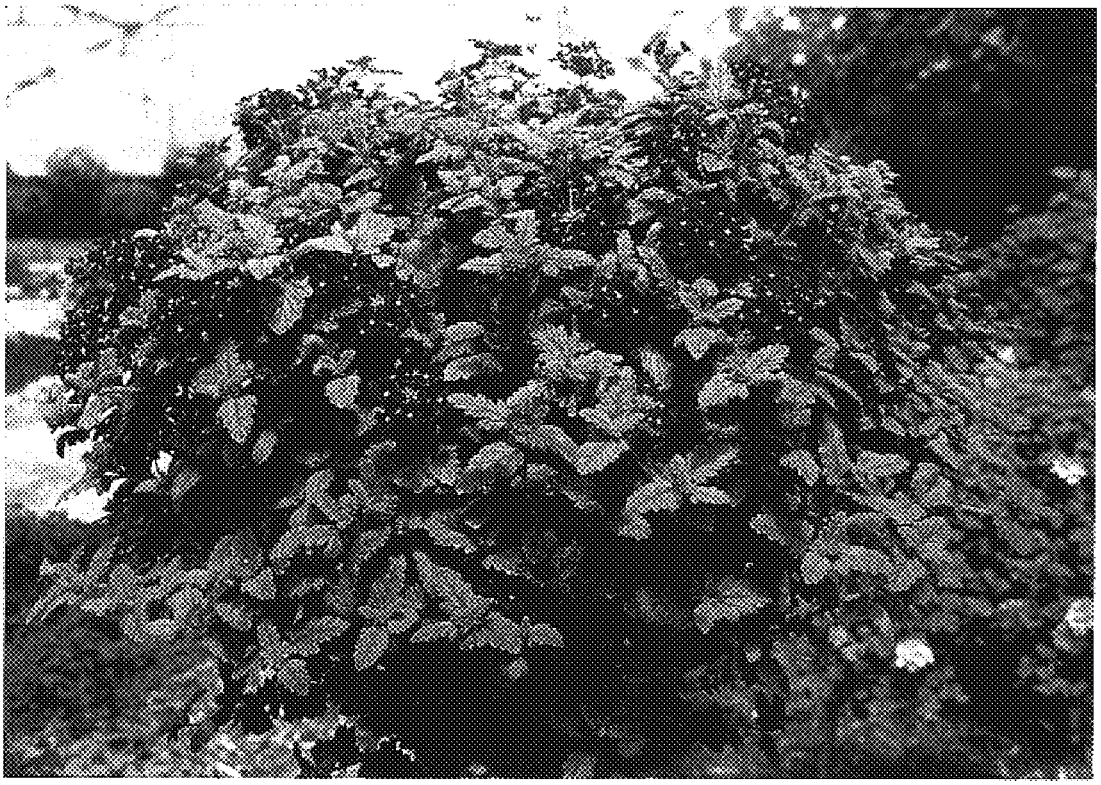
FIG. 1 illustrates a typical plant of the new variety of *Verbena* plant 'Sunmaribagadi'.
Figure 2:
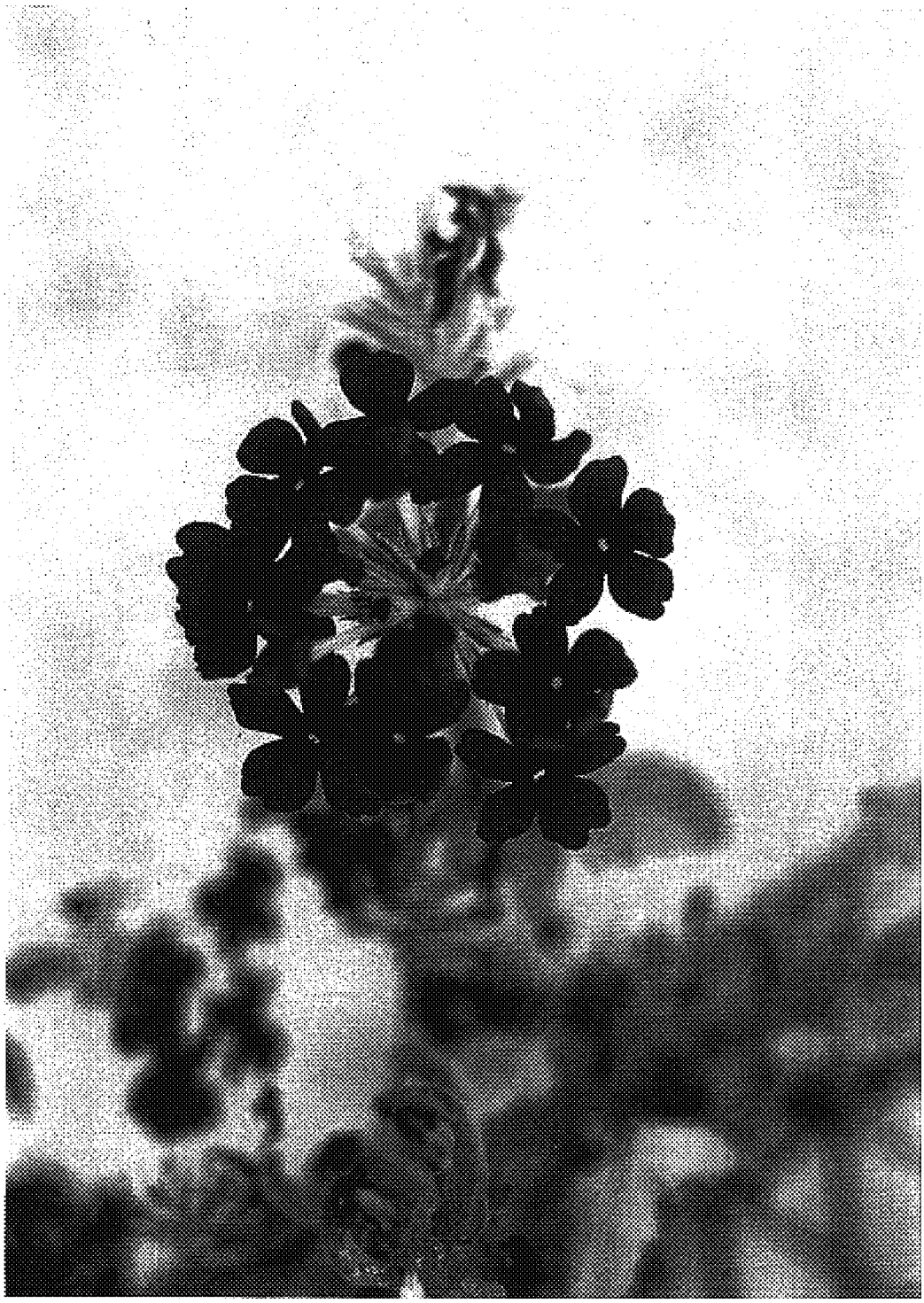
FIG. 2 illustrates a close view of typical blossoms of the new variety of *Verbena* plant 'Sunmaribagadi'.

The botanical characteristics of the new and distinct variety of *Verbena* plant named 'Sunmaribagadi' are as follows when observed during October at Yokaichi-shi, Shiga-ken, Japan, at an age of 6 months.

Plant:
- *Growth habit.*—Decumbent.
- *Plant width.*—Approximately 60–70 cm.
- *Plant height.*—Approximately 26 cm.

Stem:
- *Diameter.*—Approximately 2.0–3.0 mm.
- *Anthocyanin pigmentation.*—Absent.
- *Pubescence.*—Dense.
- *Prickles.*—Absent.
- *Branching.*—Abundant.
- *Subterranean stem.*—Absent.
- *Length of internode.*—Approximately 1.4–2.5 cm.

Leaf:
- *Phyllotaxis.*—Opposite.
- *Shape of blade.*—Hastate.
- *Apex shape.*—Obtuse.
- *Base shape.*—Truncate.
- *Margin.*—Serrate.
- *Depth of blade incision.*—Shallow.
- *Length.*—Approximately 2.5–2.8 cm.
- *Width.*—Approximately 1.0–1.3 cm.
- *Color.*—Adaxial side: Near R.H.S. 137A (Dark olive green); Abaxial side: Near R.H.S. 144B.
- *Pubescence.*—Dense.
- *Petiole.*—Absent.

Flower:
- *Shape of cluster.*—Obconical.
- *Cluster length.*—Approximately 1.7–2.7 cm.
- *Cluster diameter.*—Approximately 3.9–5.0 cm.
- *Facing direction.*—Upward.
- *Floret diameter.*—Approximately 1.5–1.7 cm.
- *Floret length.*—Approximately 1.7–1.9 cm.
- *Color of petal.*—Adaxial side: Near R.H.S. 59A (Dark purplish red); Abaxial side: Near R.H.S. 59C.
- *Eye color.*—Absent.
- *Variegation.*—Absent.
- *Petal apex.*—Emarginate.
- *Number of petals.*—Generally 5.
- *Calyx length.*—Approximately 0.8–1.0 cm.
- *Calyx shape.*—Tubular. Sepals have an acute apex and are fused at the base.
- *Reproductive organs.*—1 pistil and 4 stamens.
- *Pistil shape.*—Bifid.
- *Anther color.*—Near R.H.S. 1B (Yellow green).
- *Filament color.*—Near R.H.S. 1B (Yellow green).
- *Pollen.*—Present in a moderate quantity, color near R.H.S. 11D.
- *Stigma color.*—Near R.H.S. 4D.
- *Style color.*—Near R.H.S. 144B.
- *Ovaries.*—Commonly four in number.
- *Peduncle diameter.*—Approximately 1.5–2.0 mm.
- *Peduncle length.*—Approximately 1.0–3.0 cm.
- *Peduncle color.*—Near R.H.S. 137C.
- *Number of flowers.*—Approximately 17.
- *Flower fragrance.*—Absent.
- *Flowering time.*—Early.
- *Flowering period.*—April to November in the southern Kanto area, Japan. The plant shape does not change throughout this period. A typical flower commonly lasts 5 to 7 days on the plant when experiencing a temperature of approximately 20° C.
- *Fruit and seed.*—Fruit and seed production has not been observed.

Physiological and ecological characteristics:
- *Winter hardiness.*—USDA Hardiness Zone 4–9 (Grown as perennial).
- *Heat tolerance.*—The plant grows well at temperatures up to at least 35° C.
- *Disease and pest resistance.*—Resistant to powdery mildew. No serious damage by pathogens and pests common to *Verbena* has been observed.

It is claimed:

1. A new and distinct variety of *Verbena* plant named 'Sunmaribagadi', substantially as herein illustrated and described.

* * * * *